United States Patent
Tsukashima

(10) Patent No.: US 11,759,629 B2
(45) Date of Patent: Sep. 19, 2023

(54) UNIDIRECTIONAL ELECTRODE AND METHOD FOR STIMULATION OF THE SUBTHALAMIC NUCLEUS OF THE BRAIN

(71) Applicant: Sensoria Therapeutics, Inc., Irvine, CA (US)

(72) Inventor: Ross Tsukashima, Irvine, CA (US)

(73) Assignee: Sensoria Therapeutics, Inc., Irvine, CA (US)

( * ) Notice: Subject to any disclaimer, the term of this patent is extended or adjusted under 35 U.S.C. 154(b) by 0 days.

(21) Appl. No.: 17/677,609

(22) Filed: Feb. 22, 2022

(65) Prior Publication Data

US 2022/0273943 A1 Sep. 1, 2022

Related U.S. Application Data

(60) Provisional application No. 63/154,559, filed on Feb. 26, 2021.

(51) Int. Cl.
*A61N 1/36* (2006.01)
*A61N 1/05* (2006.01)
*A61B 17/34* (2006.01)

(52) U.S. Cl.
CPC ........ *A61N 1/0534* (2013.01); *A61B 17/3468* (2013.01); *A61N 1/36182* (2013.01)

(58) Field of Classification Search
CPC .............. A61N 1/0534; A61N 1/36182; A61B 17/3468
See application file for complete search history.

(56) References Cited

U.S. PATENT DOCUMENTS

| | | | |
|---|---|---|---|
| 7,797,029 B2 | 9/2010 | Gibson et al. | |
| 9,327,107 B2 | 5/2016 | Moffitt | |
| 10,052,478 B2 | 8/2018 | Greenburg et al. | |
| 10,130,814 B2 | 11/2018 | Gill | |
| 2011/0264165 A1* | 10/2011 | Molnar | A61N 1/36185 607/45 |
| 2012/0215218 A1* | 8/2012 | Lipani | A61N 1/36178 606/41 |
| 2016/0051812 A1* | 2/2016 | Montgomery, Jr. | A61B 5/377 607/116 |
| 2018/0125585 A1 | 5/2018 | Mechael et al. | |

OTHER PUBLICATIONS

International Search Report and Written Opinion dated May 3, 2022 from IA PCT/US2022/017745.
Hamid, et al., Targeting the subthalamic nucleus for deep brain stimulation: technical approach and fusion of pre- and postoperative MR images to define accuracy of lead placement, J Neurol Neurosurg Psychiatry 2005;76:409-414, Feb. 16, 2005.

* cited by examiner

*Primary Examiner* — Eric D. Bertram
(74) *Attorney, Agent, or Firm* — Crockett & Crockett, PC; K. David Crockett, Esq.; Niky Economy Syrengelas, Esq.

(57) ABSTRACT

A unidirectional electrode and method for sensing and stimulating the subthalamic nucleus of the brain to treat certain disorders such as epilepsy, Parkinson's, essential tremors and dystonia.

4 Claims, 6 Drawing Sheets

Horizontal View

Fig. 3  Horizontal View

Horizontal View

UNIDIRECTIONAL ELECTRODE AND METHOD FOR STIMULATION OF THE SUBTHALAMIC NUCLEUS OF THE BRAIN

This application claims priority to U.S. Provisional Application 63/154,559, filed Feb. 26, 2021, the entirety of which is incorporated herein by reference.

FIELD OF THE INVENTIONS

The inventions described below relate to the field of electrode assemblies for stimulation of the subthalamic nucleus of the brain.

BACKGROUND OF THE INVENTIONS

Deep brain stimulation (DBS) technology has shown promise for treatment of movement and affective disorders such as Parkinson's disease, epilepsy, essential tremor and dystonia. Deep brain stimulation is accomplished by placing a neurostimulation lead connected to a pulse generator within the brain, near or contacting the brain structures such as the subthalamic nucleus (STN) that control motor functions. Typical treatment protocols use cylindrical probes with electrode assemblies disposed on the distal tip of the probes. The electrode assembles include circumferential electrodes or a number of electrodes arranged around the circumference of cylindrical probe, and provide omnidirectional or limited directional stimulation due to the cylindrical shape of the electrode of brain tissue proximate the tip of a probe. The electrodes on the tip of the probe may be placed in various locations within the brain, and may be operated to stimulate various parts of the brain. Because the circumferential electrodes or electrode arrays of the prior art provide omnidirectional or partial omnidirectional stimulation, they may stimulate structures in the brain to uncertain or undesired effect while stimulating desired structures to achieve a desired effect. For example, common side effects during lateral stimulation in STN-DBS include focal muscle contraction and dysarthria as a result of corticobulbar tract activation. There is a need for an electrode assembly that can stimulate desired areas but also simultaneously avoid stimulation of other non-targeted areas within the brain.

Additionally, cylindrical electrode assemblies are hard to place within the brain. The cylindrical electrode assemblies are prone to rotation or spinning and it can also be difficult to determine which parts of the electrode assemblies are live when placed within the brain. Also, the cylindrical electrodes can migrate back and forth within the brain once implanted instead of remaining securely positioned within the brain. Thus, there is a need for an electrode assembly that allows accurate electrode assembly placement within the brain. Also, there is a need for an electrode assembly that provides for better visualization, works easier under MRI, and is placed and oriented easier than previous electrode assemblies.

SUMMARY

The devices and methods described below provide for improved deep brain stimulation treatment using an electrode assembly that allows for stimulation of desired areas but also simultaneously avoids stimulation of non-targeted areas of the brain. The electrode assembly includes a housing having a first face and a second face. The first face includes a multi-electrode array, where voltage can be applied through the electrodes of the electrode assembly to tissue proximate the electrodes. The second face is insulated so that no voltage differential is applied to tissue proximate the second face in order to prevent stimulation to certain parts of the brain. The electrode assembly has an asymmetrical cross sectional shape in a transverse axis of the electrode assembly and may be paddle-shaped in order to prevent the rotation, migration or spinning of the electrode assembly when installed in the brain. Alternatively, the electrode assembly may be triangle or rectangular shaped to allow for selective activations to one side, two sides or all three sides for circumferential activations.

The device, and the method of stimulation it enables, may be used during the course of deep brain stimulation treatments. The STN is one of the target nuclei for deep brain stimulation for treatment of certain disorders including epilepsy, Parkinson's, essential tremors and dystonia. A preferred electrode assembly placement may be within the brain of a patient with the first face of the electrode assembly proximate to and facing the posterolateral sensorimotor region of the subthalamic nucleus and the second insulated and non-conductive face proximate to and facing the internal capsule (such that the electrode assembly is place with the STN between the electrode assembly and the internal capsule, or between the STN and the thalamus). The conductive face of the electrode assembly is proximate the STN and the insulated face faces the internal capsule, the thalamus or other non-targeted tissue. An alternative electrode assembly placement will be within the brain of the patient with the first face of the electrode assembly within the posterolateral sensorimotor portion of the subthalamic nucleus and with the second insulated and non-conductive face facing away from the subthalamic nucleus, toward the internal capsule or the thalamus. Another alternative electrode assembly placement will be within the brain of a patient with the first face of the electrode assembly proximate to and facing the posterolateral sensorimotor portion of the subthalamic nucleus and with the second insulated and non-conductive face facing away from the subthalamic nucleus, toward the internal capsule or the thalamus (such that the electrode assembly is disposed between the STN and the internal capsule or the thalamus).

DETAILED DESCRIPTION OF THE INVENTIONS

Figure 1:
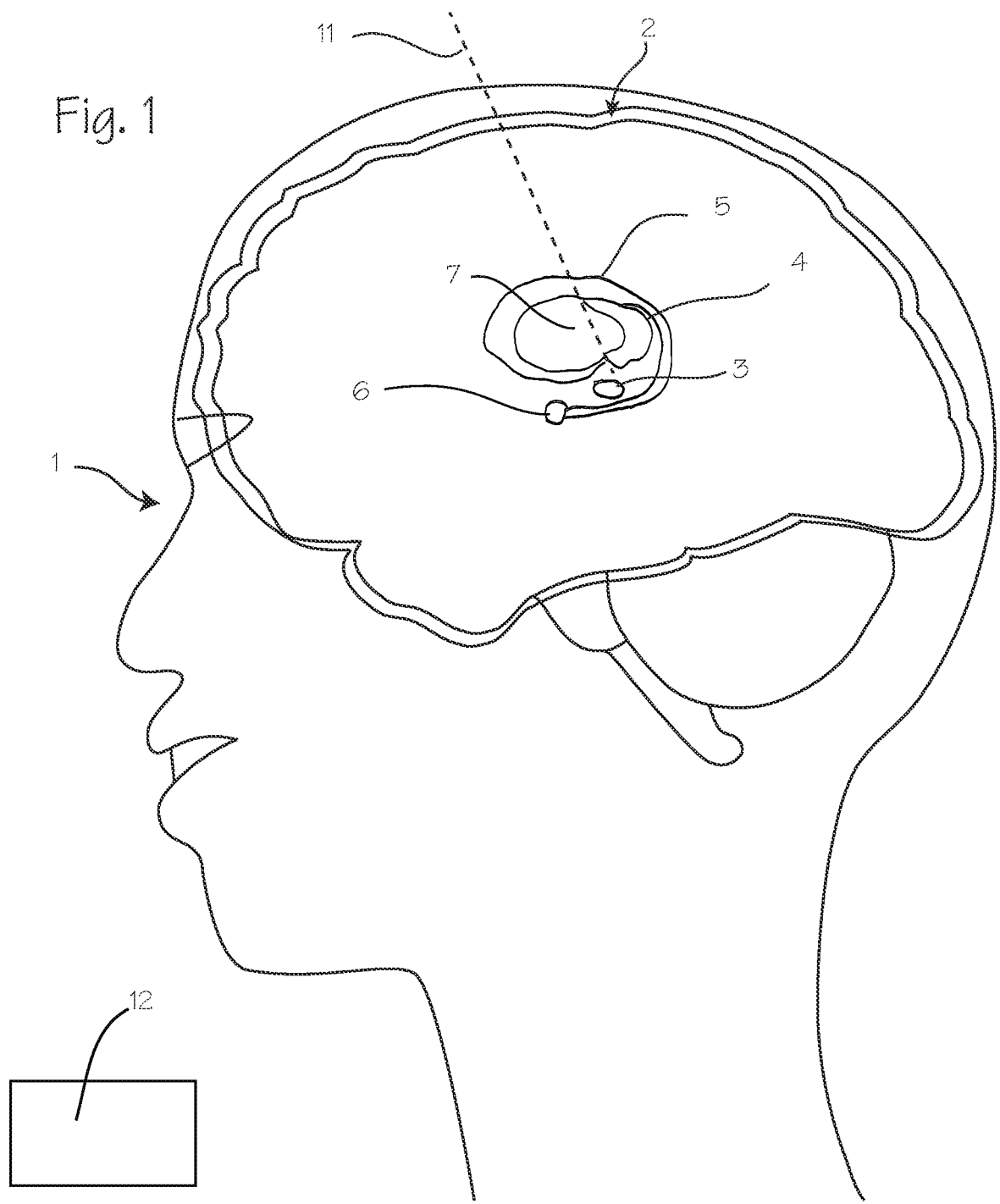
FIG. 1 is a lateral view of a patient's brain.

FIG. 1 is a lateral view of a patient 1 with a condition requiring deep brain stimulation (DBS) of the brain 2. Structures within the brain such as the subthalamic nucleus (STN) 3, thalamus 4, caudate nucleus 5, amygdala 6 and putamen 7 are shown. FIG. 1 shows the placement of a "unidirectional" electrode assembly 8 (shown in FIG. 2) within the brain of the patient. The electrode assembly is installed in the brain with the STN between the electrode assembly and the thalamus, or, alternatively with the electrode assembly between the STN and the thalamus, with the electrode assembly facing the STN. The electrode assembly can also be installed in the brain with the STN between the electrode assembly and the internal capsule, or, alternatively with the electrode assembly between the STN and the internal capsule, with the electrode assembly facing the STN. The electrode assembly includes a first face 9 (shown in FIG. 2) with an electrode array operable to induce a voltage along the conductive electrode face. The electrode assembly also includes a second insulated face 10 (shown in FIG. 2) where no voltage or current flows through the insulated face. The electrode assembly may be implanted in the brain with the conductive face in apposition to the posterolateral sensorimotor portion of the STN, and with the insulated face in apposition to either the thalamus in the first placement, or the internal capsule in the second placement, or other structure of the brain which is preferably protected from stimulation, so that no undesired voltage differential is induced across non-targeted tissue. The electrode assembly is inserted along insertion line 11. A controller 12 external to the skull may be used to control operation of the electrode assembly.

Figure 2:
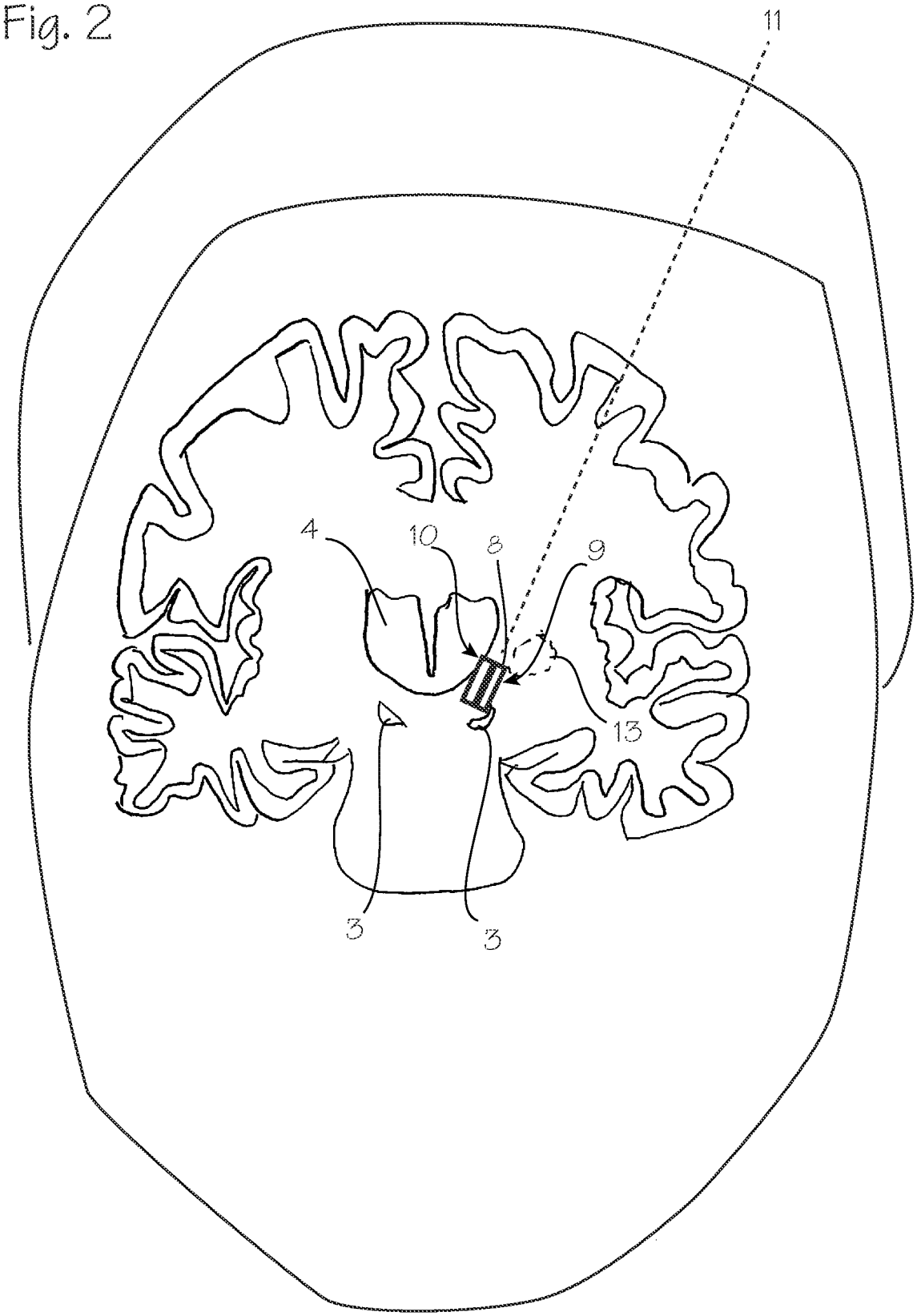
FIG. 2 is a coronal view of a patient's brain illustrating a first electrode assembly placement.

FIG. 2 is a coronal view of a patient's brain illustrating a first electrode assembly placement. It shows placement of the electrode assembly relative to the thalamus 4 and the STN 3 in a frontal plane. As shown in FIG. 2 the electrode assembly has been inserted along insertion line 11 through the brain until the electrode array and conductive face 9 of the electrode assembly is proximate to the STN and faces the STN and the insulated face 10 faces (is in apposition to) the thalamus 4. This figure illustrates that there are 2 different STN's and line 11 illustrates the insertion pathway to the placement between one of the STN's and the thalamus 4. The electrodes of the electrode assembly first face are operable, when energized, to induce a stimulating voltage to the STN while the second face prevents or limits application or stimulating voltage to the thalamus.

Figure 3:
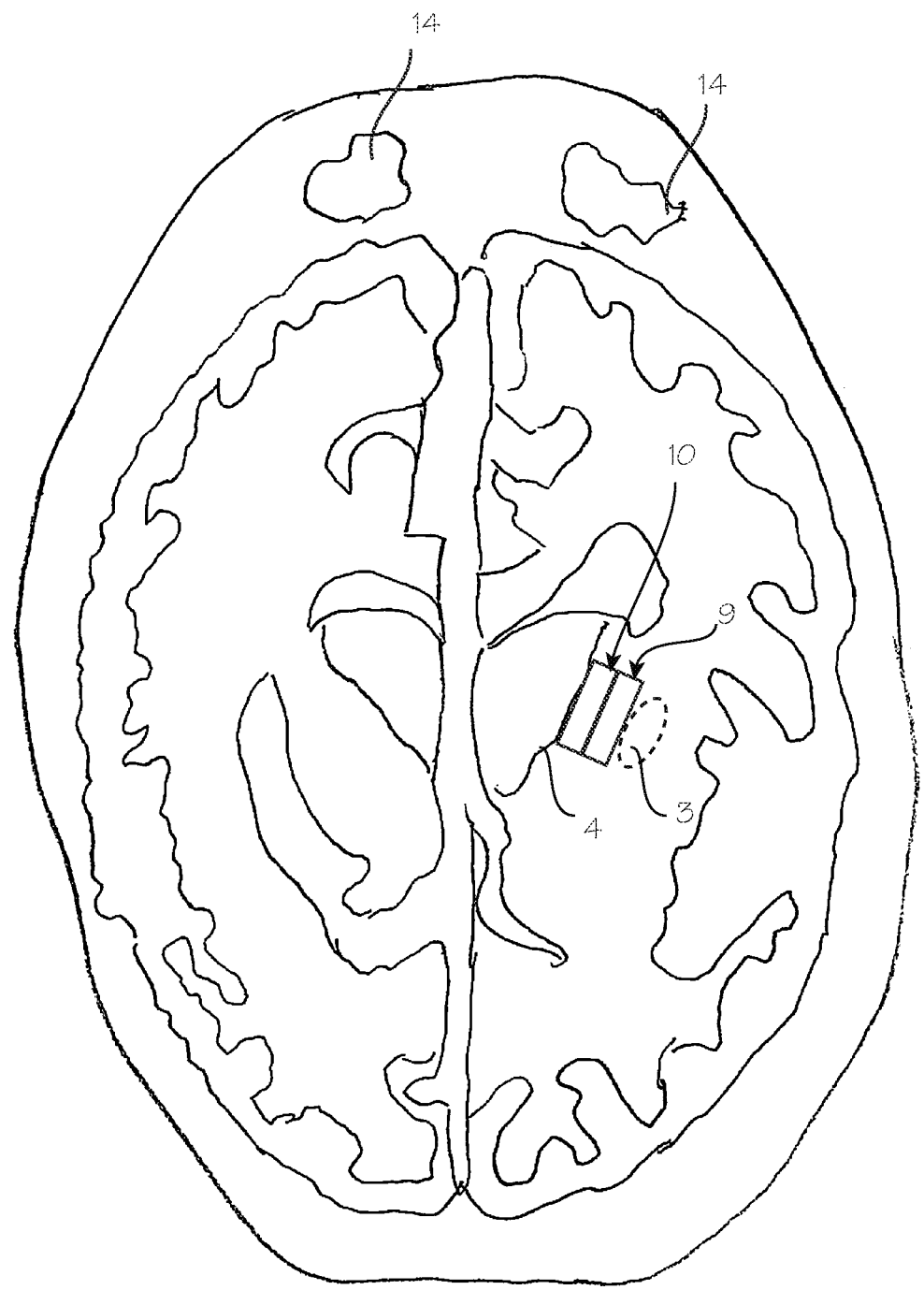
FIG. 3 is a horizontal cross-sectional view of a patient's brain illustrating a first electrode assembly placement.

FIG. 3 is a horizontal cross-sectional view of a patient's brain illustrating a first electrode assembly placement. The electrode assembly is illustrated placed relative to the thalamus and STN. The patient eyes 14 are illustrated in order to orient front to back of the brain. In this view, the electrode assembly has been placed laterally to the thalamus 4, with the electrode array and conductive face 9 of the electrode assembly proximate the STN 3 and facing the STN, and the insulated face 10 of the electrode assembly facing the thalamus 4. The electrode assembly is implanted so that the electrode array of the electrode assembly is in apposition to the STN and the insulated electrode face is in apposition between the thalamus. The thalamus is visible in this plane but the STN is not so it is shown in phantom.

Figure 4:
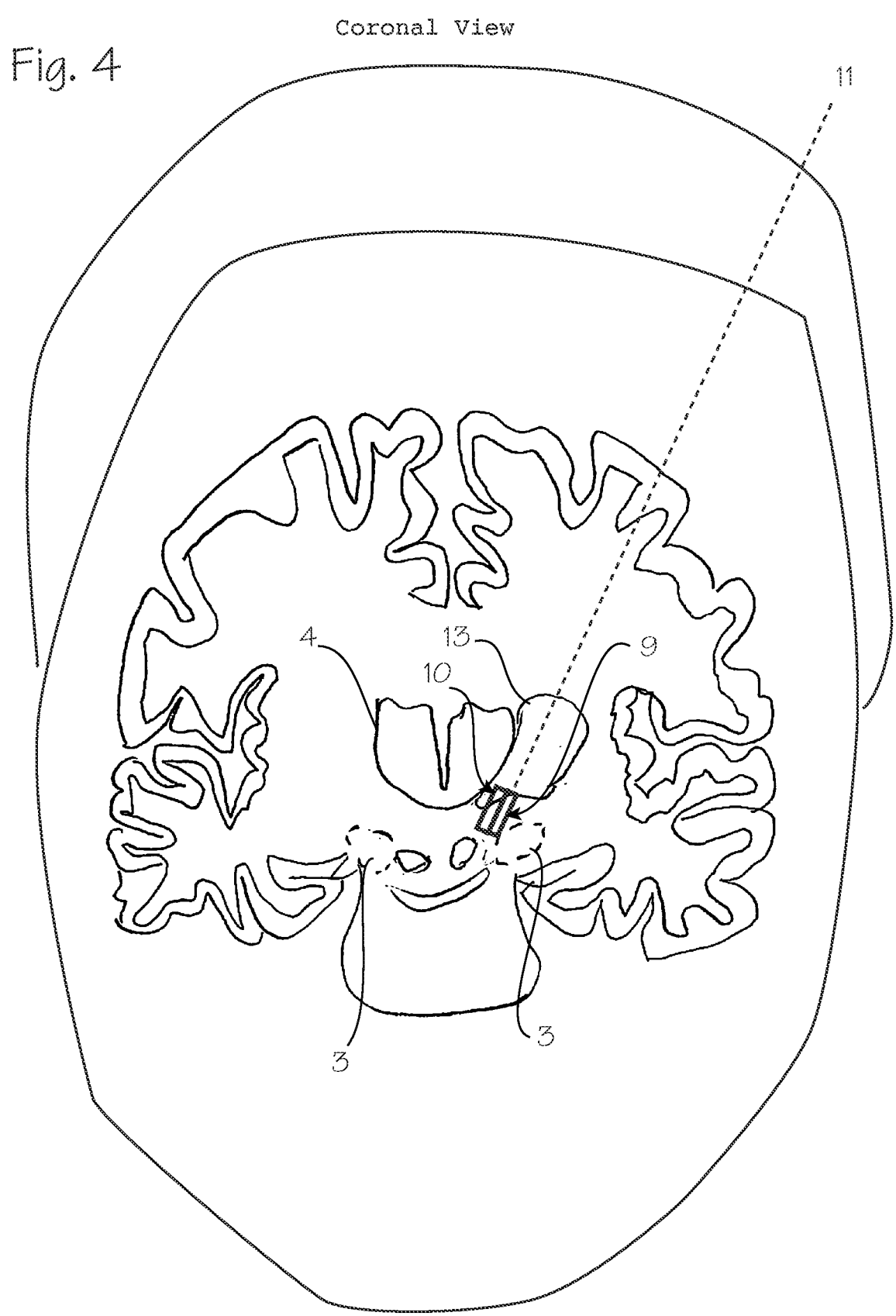
FIG. 4 is a coronal view of a patient's brain illustrating a second electrode assembly placement.

FIG. 4 is a coronal view of a patient's brain illustrating a second electrode assembly placement. It shows placement of the electrode assembly relative to the internal capsule 13 and the STN 3 in a frontal plane. As shown in FIG. 4 the electrode assembly has been inserted along insertion line 11 through the brain until the electrode array and conductive face 9 of the electrode assembly is proximate to the STN and faces the STN and the insulated face 10 faces (is in apposition to) the internal capsule 13. This figure illustrates that there are 2 different STN's and line 11 illustrates the insertion pathway to the placement between one of the STN's and the internal capsule 13. The electrodes of the electrode assembly first face are operable, when energized, to induce a stimulating voltage to the STN while the second face prevents or limits application or stimulating voltage to the internal capsule 13. The electrodes of electrode assembly first face are operable, when energized, to induce a stimulating voltage to the STN while the second face prevents or limits application of stimulating voltage to the internal capsule or other structures proximate the electrode assembly.

Figure 5:
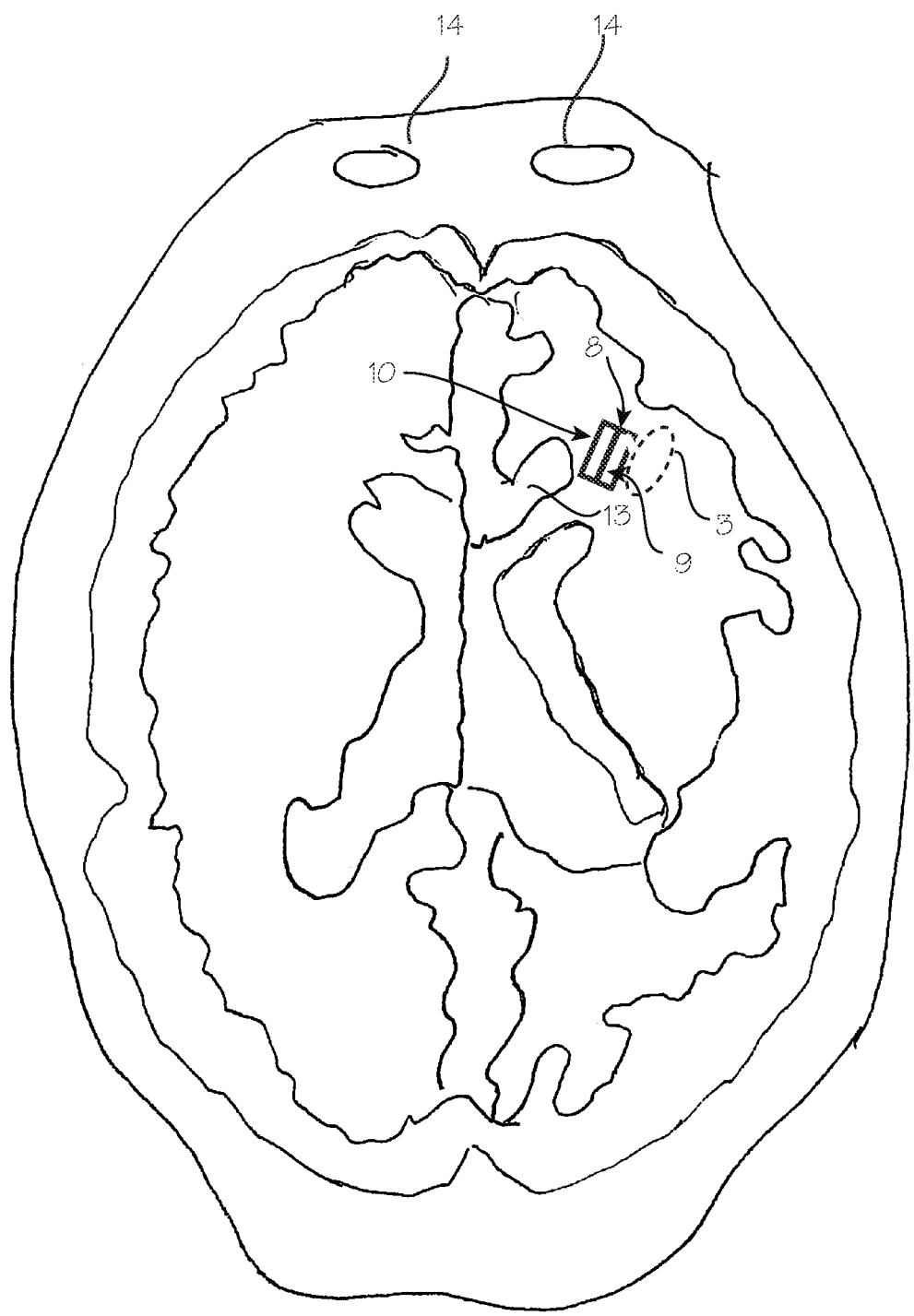
FIG. 5 is a horizontal cross-sectional view of a patient's brain illustrating a second electrode assembly placement.

FIG. 5 is a horizontal cross-sectional view of a patient's brain illustrating a second electrode assembly placement. The electrode assembly is illustrated placed relative to the internal capsule and STN. The electrode assembly is placed laterally to the internal capsule 13, with the electrode array and conductive face 9 of the electrode assembly proximate the STN 3 and facing the STN, and the insulated face 10 of the electrode assembly facing the internal capsule 13.

Figure 6:
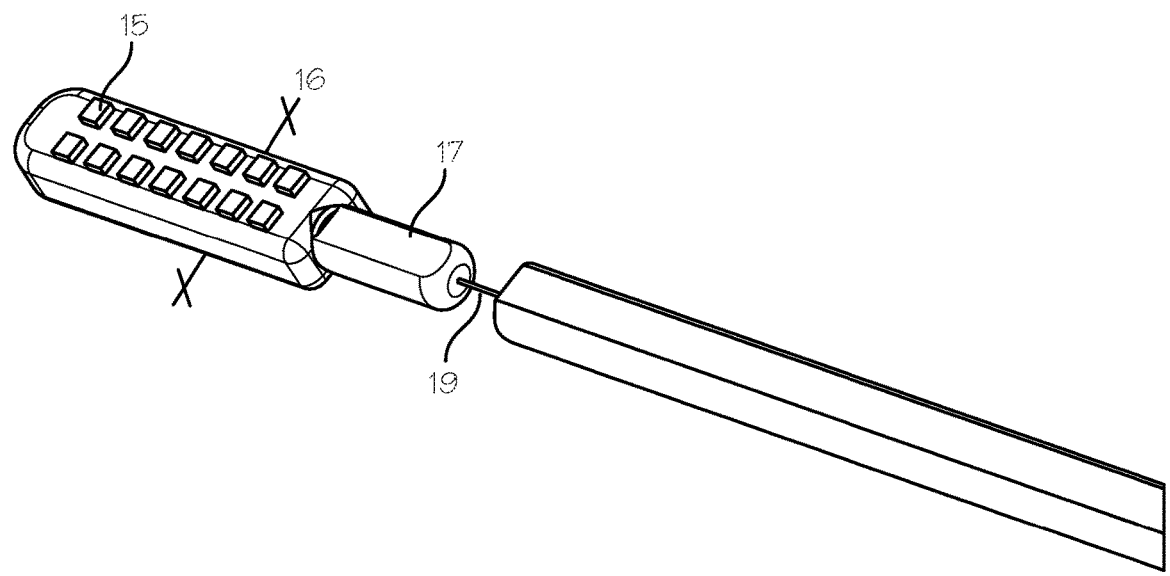
FIG. 6 illustrates an electrode assembly in detail.

FIG. 6 illustrates the electrode assembly in detail. The electrode assembly includes a housing having a first face 9 and a second face 10. The first face includes at least one electrode 15, though preferably comprises a multi-electrode array, whereby voltage can be applied through the electrode of the electrode assembly to tissue proximate the electrode (s). The second face is insulated so that no voltage differential is applied to tissue proximate the second face in order to protect any part of the brain that is proximate the second face, for which stimulation is undesirable. The electrode assembly has an asymmetrical cross sectional shape in a transverse axis 16 of the electrode assembly to prevent rotation of the electrode assembly after placement. The electrode assembly may be paddle-shaped in order to prevent the migration of the electrode assembly when installed in the brain. Alternatively, the electrode assembly may be square, triangle, rectangle or other non-symmetrical or non-round shape. The electrode assembly may include an mounting plug 17, with any non-circular transverse cross-section, so that is may fit into a socket of matching cross section in a delivery tube 18. The delivery tube may be used to push the electrode through the brain, through an access burr-hole in the skull, into the desired position. The delivery rod may has a rectangular shape, indicia, or other means for registration of the electrode face relative to the proximal end of the delivery rod, so aid placement into the brain with the electrode face directed as desired. Thus, the delivery tube is keyed to the electrode assembly to keep the electrode face and proximal face and proximal end of the delivery rod registered. The housing of the electrode assembly can be made of various non-metallic materials including glassy or pyrolytic carbon, graphene, doped silicon, germanium or other specially fabricated conductive polymers. Alternatively, the electrode assembly can be made of other metallic or conductive thin films.

The electrode assembly in FIG. 6 is an asymmetrical electrode with multiple conductive elements 15 on the first face of the electrode. This Figure illustrates a 2 row by 7 column array of electrodes on the first face where the top left square represents electrode [1,1] and the bottom right electrode represents electrode [2,7]. The electrodes can be activated to stimulate the STN in a multitude of combinations. For example, electrode squares [1,1] and [1,2] could be activated to create a small zone of bipolar stimulations between those 2 electrodes. Alternatively, electrode [1,1] and [1,2] could be connected together as a set to create a rectangular shape to be used with the square pair electrodes [2,1] and [2,2], again in bipolar operation. Alternatively, one or several of the electrodes could be energized with the same polarity and used as a monopolar electrode, in conjunction with a surface electrode on the scalp or elsewhere. The second face of the electrode assembly need not contain any electrodes and need only contain insulated material that presents voltage applied across the second face. Alternatively, the electrode assembly can include multiple conductive elements on both the first face and the second face of the electrode. The first face and the second face can include a multi-electrode array, whereby voltage can be applied through selected electrodes of the electrode assembly, creating either monopolar or bipolar stimulation depending on the arrangement of the connections to the electrodes.

Figure 7:
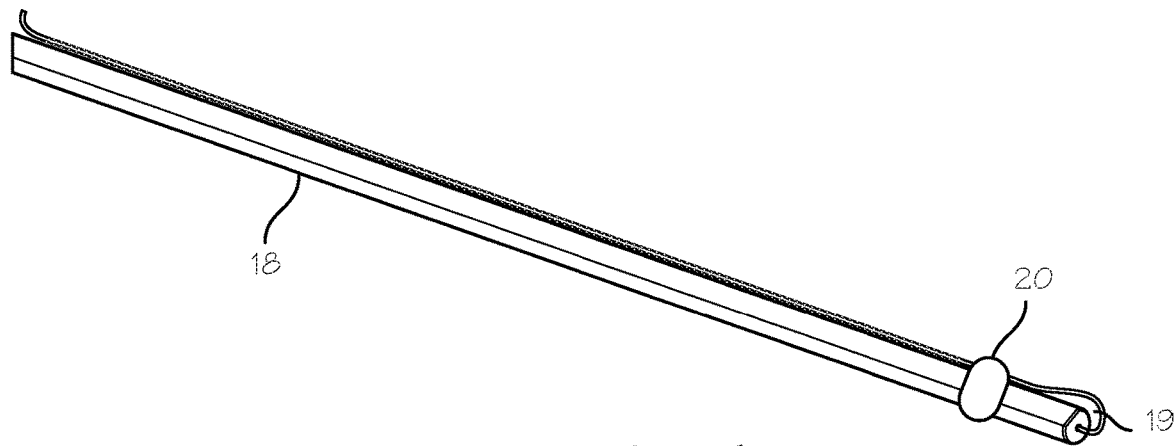
FIG. 7 illustrates a delivery tube and tether used with the electrode assembly.

FIG. 7 illustrates a delivery tube and tether such as a conductive or non-conductive thread 19 connected to the electrode assembly, used to hold or release the electrode or to connect the electrode to other electrodes. Optionally a clip 20 may be included on the delivery tube to engage the tether to the delivery tube to retain the electrode in place once inserted into the brain. If the clip is removed, the delivery tube can be removed to leave the electrode and tether in place. The tether can be used for electrode delivery, to reduce the possibility of movement of the brain by allowing ingrowth of brain tissue in the tether, anchoring the electrode in place. It can also be used for removal of the electrode from the brain when required by pulling on the tether end. Alternatively, the tether could be connected to other electrode tethers in order to allow the multiple electrodes to create an electrical network or return path for monopolar stimulation.

In use, a surgeon will use a delivery tube to implant the unidirectional electrode assembly within the brain of a patient so that the first face of the electrode assembly is proximate to the posterolateral sensorimotor portion of the STN and the second face faces away from the STN, toward the internal capsule or other nearby structure. Alternatively, the electrode assembly can be positioned so that the first face of the electrode is proximate the posterolateral sensorimotor STN and the second face faces the thalamus or other structure. The delivery rod allows the surgeon to identify which way the electrode assembly is facing to ensure the conductive face is proximate the STN and the insulated face faces the internal capsule. Additional imaging and guidance, including fluoroscopy and neuronavigation, may be used to assist in placement of the electrode array. Alternatively, this delivery method can be used with placement of unidirectional electrode assemblies and devices.

Alternatively, the electrode assembly can include multiple conductive elements on both the first face and the second face of the electrode. The first face and the second face can include a multi-electrode array, whereby voltage can be applied through selected electrodes of the electrode assembly to stimulate desired areas and insulate other areas where stimulation is undesirable.

After the electrode assembly is implanted, a controller 12 external to the skull, with a transmitter assembly programmed to provide signals and power to the electrode array of the electrode assembly, may be used to control operation of the electrode array to provide electrical stimulation to the STN, which may be limited to the posterolateral sensorimotor STN. The transmitter is operated to provide power to the electrode assembly and transmit control signals to the electrodes, as desired to affect symptoms of a disease subject to stimulation by the electrode. The electrode signals are native brain signals from the patient brain that are indicative of a motor deficiency. Power is applied at a therapeutically effective rate in order to treat certain disorders such as epilepsy, Parkinson's, essential tremors and dystonia. Stimulation levels may be within the following ranges: amplitude can range between 0.1 mA to 12.75 mA, the maximum output voltage can be less than 6.5V, the pulse width range can be 10 µs to 500 µs, and the frequency can range 2 Hz to 240 Hz. Stimulation leveal can also range between 0.0 mA to 25.5 mA (for current) or 0.0V to 10.5V (for voltage), the pulse width range can be 60 µs to 450 µs, and the frequency can range 2 Hz to 240 Hz. These electrodes can also be used for sensing impulses to aid in targeting the best contact points from the STN.

The electrode may use an implantable pulse generator as the electrical source to cause voltage to flow through an extension wire to the first face of the electrode, across the electrode and back through the tissue to the implantable pulse generator. Deep brain stimulation requires operation of the implantable pulse generator into different stimulation modes, such as monopolar, bipolar, tripolar, double monopolar. The preferred electrode polarity can be either monopolar or bipolar. In monopolar stimulation there is one electrode and the return electrode is the implantable pulse generator. In bipolar stimulation there are two electrodes, one the anode and the other the cathode. Once the electrode is implanted into a target site, the electrode extension wire connects the electrode to the implantable pulse generator. The implantable pulse generator then causes voltage to flow to the first face of the electrode, across the electrode and back through the tissue to the implantable pulse generator.

Thus, devices may be used in a method that entails performing deep brain stimulation on a patient's brain by implanting an electrode assembly between an STN and a second structure of the brain to be protected from stimulation, with a first region of the electrode assembly comprising an array of electrodes disposed proximate to and in apposition to the STN and a second region of the STN comprising an electrically insulative material disposed proximate to and in apposition to the structure of the brain to be protected from stimulation, and then applying a stimulating voltage, through the electrode array, to the STN, without applying a stimulating voltage to the structure of the brain to be protected from stimulation. The electrode assembly does not need to actually contact the STN, the placement of the electrode assembly must merely allow for stimulation of one region of the STN, while also minimizing or avoiding stimulation of other regions of the STN.

Placement of the stimulating electrodes on the first face of the electrode assembly preferably contacts the center of the STN in order to produce the best outcome. Alternatively, adjacent structures can also be used as placement targets. To access the STN, a surgeon selects a target within the STN and aims to select a safe trajectory that avoids intersecting other structures. A trajectory matrix is formulated over the skull of the patient where all trajectories converge towards the STN target point. Each trajectory can be described using two angles, the coronal and the sagittal planes, corresponding to the arc and ring of a Cosman-Robert-Wells stereotactic frame, respectively. The coronal angles are between 0° and 30° from the vertical and the sagittal angle are between 10° and 45° from the vertical plane. An example of a final target structure, after trajectory recordings can be 11.7 mm lateral, 2.1 mm posterior, and 3.8 mm inferior to the center of an AC-PC line. Alternatively, the final target structure can be 11.8 mm lateral, 2.4 mm posterior, and 3.7 mm inferior to the center of the AC-PC line. Alternative methods of placing the electrodes can further include placement through the use of computerized neuro navigation hardware or software.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A method of performing deep brain stimulation on a patient's brain, said method comprising the steps of:
    implanting an electrode assembly between a subthalamic nucleus and an internal capsule of the brain to be protected from stimulation, with a first region of the electrode assembly comprising an array of electrodes disposed proximate to and in apposition to the subthalamic nucleus and a second region of the electrode assembly comprising an electrically insulative material disposed proximate to and in apposition to the internal capsule to be protected from stimulation;
    applying a stimulating voltage, through the electrode array, to the subthalamic nucleus, without applying a stimulating voltage to the internal capsule;
    wherein the step of implanting an electrode assembly between a subthalamic nucleus and the internal capsule further comprises insertion to a target structure after trajectory recordings of 11.7 mm lateral, 2.1 mm posterior, and 3.8 mm inferior to the center of an AC-PC line.

2. The method of claim 1 further comprising the step of:
placing the array of stimulating electrodes on the first face of the electrode assembly to contact the center of the subthalamic nucleus;
providing a controller with a transmitter assembly programmed to provide signals and power to the array of stimulating electrodes.

3. The method of claim 1 further comprising the step of:
providing a transmitter assembly external to the skull, programmed to provide signals and power to the electrode array of the electrode assembly; and
operatively controlling the electrode array to provide electrical stimulation to the subthalamic nucleus.

4. The method of claim 1 further comprising the step of:
using a delivery tube to implant the electrode assembly within the brain.

* * * * *